(12) United States Patent
Nishimura et al.

(10) Patent No.: US 8,309,119 B2
(45) Date of Patent: Nov. 13, 2012

(54) DRUG CONTAINING ADHESIVE PREPARATION

(75) Inventors: Masato Nishimura, Ibaraki (JP); Sachiko Terashi, Ibaraki (JP); Shiro Satoda, Ibaraki (JP); Keigo Inosaka, Ibaraki (JP); Kensuke Matsuoka, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 165 days.

(21) Appl. No.: 12/071,867

(22) Filed: Feb. 27, 2008

(65) Prior Publication Data

US 2008/0206315 A1    Aug. 28, 2008

(30) Foreign Application Priority Data

Feb. 28, 2007   (JP) .................. 2007-050379

(51) Int. Cl.
  *A61K 9/70*   (2006.01)
  *A61K 31/4468*   (2006.01)
  *A61F 13/02*   (2006.01)

(52) U.S. Cl. .............. 424/448; 424/449; 514/329

(58) Field of Classification Search .................. None
  See application file for complete search history.

(56) References Cited

U.S. PATENT DOCUMENTS

| 5,948,433 | A * | 9/1999 | Burton et al. | 424/448 |
|---|---|---|---|---|
| 6,231,883 | B1 * | 5/2001 | Inosaka et al. | 424/443 |
| 6,486,147 | B2 * | 11/2002 | Baldo et al. | 514/178 |
| 2002/0018805 | A1 * | 2/2002 | Gale | 424/449 |
| 2005/0163831 | A1 * | 7/2005 | Ikesue et al. | 424/449 |
| 2005/0214352 | A1 * | 9/2005 | Hori et al. | 424/449 |
| 2006/0165764 | A1 * | 7/2006 | Hanatani et al. | 424/448 |
| 2006/0222691 | A1 * | 10/2006 | Cantor et al. | 424/448 |
| 2007/0077282 | A1 * | 4/2007 | Shirai et al. | 424/448 |

FOREIGN PATENT DOCUMENTS

| CN | 1839796 | | 10/2006 |
|---|---|---|---|
| EP | 1 625 845 | | 2/2006 |
| EP | 1625845 | * | 2/2006 |
| EP | 1 686 162 | | 8/2006 |
| EP | 1686162 | * | 8/2006 |
| EP | 1 716 850 | | 11/2006 |
| EP | 1 925 300 | | 5/2008 |
| JP | 2006-076994 | | 3/2006 |
| WO | WO 2005/037946 | * | 4/2005 |

OTHER PUBLICATIONS

Tan et al. Pressure-sensitive adhesives for transdermal drug delivery systems. PSTT vol. 2, No. 2, pp. 60-69 (Feb. 1999).*
BASF. Oppanol® B 100, Oppanol® B 150, Oppanol® B 200. BASF Technical Information TI/ES 1417 (published Apr. 2003).*
LOTH. Vehicular influence on transdermal drug penetration. International Journal of Pharmaceutics 68 (1991) 1-10.).*
European Search Report issued May 15, 2009 in the European Application No. 08250660.1, which is a foreign counterpart of the present application.
Chinese Office Action issued Dec. 14, 2010 in corresponding Chinese Application No. 200810082016.6 with English translation.

* cited by examiner

*Primary Examiner* — Daniel Sullivan
*Assistant Examiner* — Peter Anthropolos
(74) *Attorney, Agent, or Firm* — Wenderoth, Lind & Ponack, L.L.P.

(57) ABSTRACT

The present invention aims at providing an adhesive preparation wherein a drug is sufficiently dissolved in an adhesive layer and is not easily separated from the adhesive layer even during preservation of the adhesive preparation.

The present invention provides an adhesive preparation having an adhesive layer on at least one surface of a support, wherein the adhesive layer comprises a first synthetic rubber having a viscosity average molecular weight of 1,600,000-6,500,000, a drug, an organic liquid component and a tackifier. The present invention further provides the aforementioned adhesive preparation, wherein the organic liquid component is contained in the adhesive layer in a proportion of 20 wt % or above relative to the total weight of the adhesive layer.

3 Claims, 1 Drawing Sheet

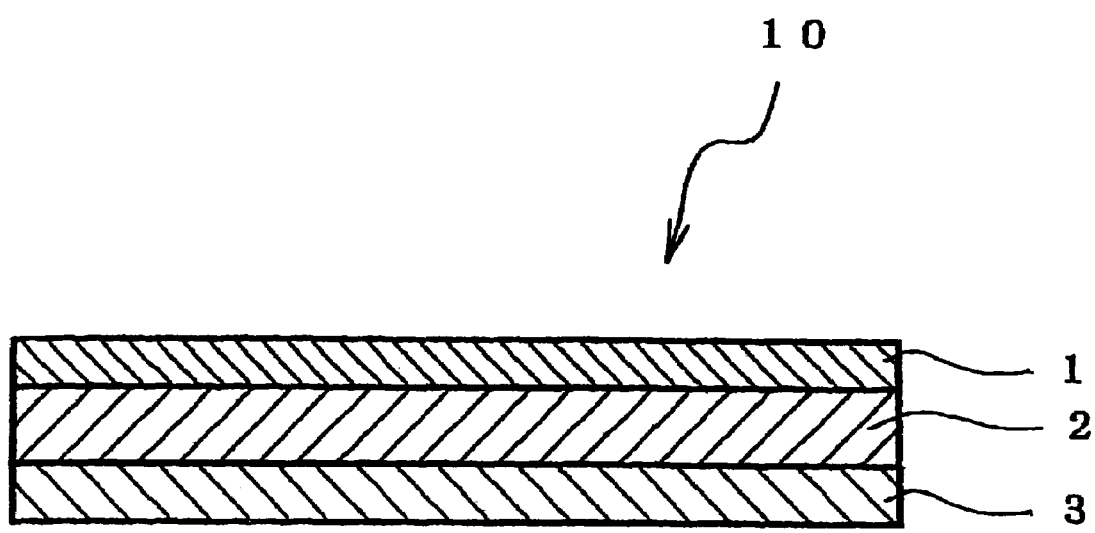

DRUG CONTAINING ADHESIVE PREPARATION

TECHNICAL FIELD OF THE INVENTION

The present invention relates to an adhesive preparation having an adhesive layer on at least one surface of a support.

BACKGROUND OF THE INVENTION

Adhesive preparations containing a drug are widely used. Since synthetic rubbers used as an adhesive do not have a functional group, they are advantageous in that the contained drug shows good stability. However, since such synthetic rubbers show low drug solubility, when a drug is contained in an adhesive layer, separation of the drug from the adhesive layer becomes a problem. For example, the following reference deals with problems relating to the dissolution of a drug in an adhesive layer.

JP-A-2006-76994 discloses an adhesive preparation containing two kinds of polyisobutylene having different molecular weights, fentanyl (drug), and fatty acid alkyl ester and long chain branched alcohol (organic liquid components).

This reference teaches that the proportion of the drug relative to the total weight of an adhesive layer is preferably not more than 2.5 wt %. This is because when a large amount of a drug is added to an adhesive layer of this kind of adhesive preparation, the drug may be separated from the adhesive layer, and this problem is yet to be improved.

To suppress separation of a drug from an adhesive layer, an organic liquid component may be added as a dissolution agent to an adhesive layer. However, when a large amount of an organic liquid component is added to an adhesive layer, the cohesion strength of the adhesive layer may decrease, and oozing during preservation of the adhesive preparation and adhesive residue on the skin upon peeling off of the adhesive preparation from the skin may be developed. In fact, this reference describes that when a proportion of an organic liquid component relative to the total weight of an adhesive layer exceeds 20%, the cohesion strength of the adhesive layer decreases markedly and a cohesive failure easily occurs. As described above, the aforementioned reference suggests difficulty associated with a large amount of an organic liquid component in an adhesive layer of such an adhesive preparation.

As is clear from the above, an adhesive preparation wherein a drug is sufficiently dissolved in an adhesive layer and is not easily separated from the adhesive layer even during preservation of the adhesive preparation has not been known.

DISCLOSURE OF THE INVENTION

In view of the above, the present invention aims at providing an adhesive preparation wherein a drug is sufficiently dissolved in an adhesive layer and is not easily separated from the adhesive layer even during preservation of the adhesive preparation.

Accordingly, the present invention provides:
(1) an adhesive preparation having an adhesive layer on at least one surface of a support, wherein the adhesive layer comprises a first synthetic rubber having a viscosity average molecular weight of 1,600,000-6,500,000, a drug, an organic liquid component and a tackifier;
(2) the adhesive preparation of (1), wherein the organic liquid component is contained in the adhesive layer in a proportion of 20 wt % or above relative to the total weight of the adhesive layer;
(3) the adhesive preparation of (1), or (2), wherein the adhesive layer further comprises a second synthetic rubber having a viscosity average molecular weight of 40,000-85,000;
(4) the adhesive preparation of any of (1) to (3), wherein the organic liquid component comprises two or more kinds of fatty acid alkyl esters;
(5) the adhesive preparation of (4), wherein the organic liquid component further comprises a long chain alcohol;
(6) the adhesive preparation of (5), wherein the long chain alcohol is contained in the adhesive layer in a proportion of more than 0 wt % and less than 7.5 wt % relative to the total weight of the adhesive layer; and
(7) the adhesive preparation of any of (1) to (6), wherein the drug is a solid drug.

Effect of the Invention

In the adhesive preparation of the present invention, the adhesive layer contains a first synthetic rubber having a viscosity average molecular weight of 1,600,000-6,500,000. Since an adhesive layer containing such an adhesive contains complicatedly entangled polymer chains, it can retain a large amount of an organic liquid component. Therefore, even when a drug does not easily dissolve in an adhesive layer, it can be sufficiently dissolved by adding a large amount of an organic liquid component to the adhesive layer, whereby an adhesive preparation wherein a drug is not easily separated from an adhesive layer even during preservation of the adhesive preparation can be obtained.

Moreover, since such an adhesive layer may sufficiently retain its shape even when it contains a large amount of an organic liquid component, oozing of the adhesive from an edge of the adhesive layer during preservation of an adhesive preparation, and an adhesive residue on the skin surface upon release of the adhesive preparation from the skin can be suppressed.

BRIEF DESCRIPTION OF THE DRAWINGS

FIG. 1 A sectional view showing one embodiment of the adhesive preparation of the present invention.

EXPLANATION OF SYMBOLS 1 support
2 adhesive layer
3 release liner
10 adhesive preparation

BEST MODE FOR EMBODYING THE INVENTION

The adhesive preparation of the present invention has an adhesive layer on at least one surface of a support, and the adhesive layer contains a first synthetic rubber having a viscosity average molecular weight of 1,600,000-6,500,000, drug, an organic liquid component and a tackifier.

The first synthetic rubber is not particularly limited as long as it has a viscosity average molecular weight of 1,600,000-6,500,000. Examples of include polydimethyl siloxane-resin, butyl rubber, ethylene-vinyl acetate-copolymer, ethylene-ethyl acrylate-copolymer, poly-alkylvinylether (e.g., poly-propylvinylether, poly-isopropylvinylether, poly-butylvinylether etc.), 2-methylpropene-polymer, ethylethylene-polymer, 1,2-dimethylethylene-polymer, ethylethylene-1,2-dimethylethylene-copolymer, poly-isoprene, poly-butadiene, styrene-isoprene-styrene block copolymer, styrene-butadiene-styrene block copolymer and the like. From the aspects of cost, handleability and the like, branched aliphatic hydrocarbon (e.g., 2-methylpropene-polymer, ethylethylene-polymer, 1,2-dimethylethylene-polymer and ethylethylene-1,2-dimethylethylene-copolymer) are preferable, and 2-methylpropene-polymer is particularly preferable.

Since the viscosity average molecular weight of the synthetic rubber is not less than 1,600,000 and the molecular chain is long and complicatedly entangled, a large amount of an organic liquid component can be retained. An adhesive layer containing such a synthetic rubber may sufficiently retain its shape. Particularly, a synthetic rubber having a viscosity average molecular weight of not less than 2,000,000 can sufficiently retain its shape even when an adhesive layer contains an organic liquid component in a proportion of not less than 20 wt % relative to the total weight of the adhesive layer, while retaining the organic liquid component. Since a synthetic rubber having a viscosity average molecular weight of less than 1,600,000 has low ability to retain an organic liquid component, the organic liquid component may ooze out from the adhesive layer containing the synthetic rubber. Even if oozing does not occur, the adhesive may ooze out during preservation of the adhesive preparation or the adhesive may remain on the skin surface upon release of the adhesive preparation from the skin, since the adhesive layer shows poor shape retention.

On the other hand, an adhesive layer containing a synthetic rubber having a viscosity average molecular weight exceeding 6,500,000 may have decreased skin adhesive strength or tackiness.

From such aspect, the viscosity average molecular weight of the first synthetic rubber is preferably 2,000,000-6,000,000, more preferably 2,500,000-5,500,000, most preferably 3,000,000-5,000,000.

The viscosity average molecular weight in the context of the present specification is obtained by calculating Staudinger Index ($J_0$) from the flow time of capillary 1 of a Ubbelohde viscosimeter at 20° C. according to the Schulz-Blaschke equation, and from the following formula by inserting the obtained $J_0$ value:

$$J_0 = \eta_{sp}/c(1+0.31\,\eta_{sp})\,\text{cm}^3/\text{g} \quad \text{(Schulz-Blaschke equation)}$$

$$\eta_{sp} = t/t_0 - 1$$

t: flow time of solution (by Hagenbach-couette Correction)
$t_0$: flow time of solvent (by Hagenbach-couette Correction)
c: concentration of solution (g/cm$^3$)

$$J_0 = 3.06 \times 10^{-2} \overline{Mv}^{0.65}$$

$\overline{Mv}$: viscosity average molecular weight

While the proportion of the first synthetic rubber in an adhesive layer is not particularly limited, it is preferably 5-50 wt %, more preferably 10-30 wt %, most preferably 16-20 wt %, relative to the total weight of the adhesive layer.

When the proportion of the first synthetic rubber in an adhesive layer is less than 5 wt %, the internal cohesion strength of the adhesive layer may decrease, and when it exceeds 50 wt %, the adhesive layer may become stiff and the tackiness may decrease.

When desired, the adhesive layer may further contain a second synthetic rubber having a viscosity average molecular weight of 40,000-85,000. By a combined use of a second synthetic rubber having high flowability as compared to the first synthetic rubber, separation of the first synthetic rubber from a tackifier can be prevented, and an adhesive layer can have suitable flexibility.

When the second synthetic rubber has a viscosity average molecular weight of less than 40,000, moreover, a tackifier and a second synthetic rubber have high affinity, and a tackifier and a first synthetic rubber have low affinity and they may be separated from each other. When the second synthetic rubber has a viscosity average molecular weight exceeding 85,000, furthermore, a second synthetic rubber and a first synthetic rubber have high affinity, and a tackifier and a first synthetic rubber have low affinity and they may be separated from each other.

The kind of the second synthetic rubber is independently selected from the kinds of the first synthetic rubber. While the first synthetic rubber and the second synthetic rubber may be of the same kind or different kinds, they are preferably of the same kind in view of the compatibility thereof.

While the proportion of the second synthetic rubber in an adhesive layer is not particularly limited, it is preferably 5-50 wt %, more preferably 10-40 wt %, most preferably 23-30 wt %, relative to the total weight of the adhesive layer. When the content of the second synthetic rubber in an adhesive layer is less than 5 wt %, a tackifier and a first synthetic rubber may be separated, and when it exceeds 50 wt %, the internal cohesion strength of the adhesive layer may be degraded. When desired, a tertiary synthetic rubber may be added to the adhesive layer.

The drug is not particularly limited, but one that can be administered to mammals such as human and the like through the skin thereof, namely, a transdermally absorptive drug is preferable. Specific examples thereof include general anesthetic drug, hypnotic sedative drug, antiepileptic drug, antipyretic and anti-inflammatory analgesic drug, seasick remedy, psychoneurotic drug, local anesthetic, skeleton muscle relaxant, autonomic nervous system drug, spasmolytic drug, antiparkinsonian drug, antihistamine drug, cardiac stimulant, antiarrhythmic drug, diuretic drug, hypotensive drug, vasoconstrictor, colonary vasodilator, peripheral vasodilator, anti-arteriosclerotic drug, cardiovascular drug, respiratory stimulant, antitussive and expectorant drug, hormonal drug, external medicine for purulent disease, analgesic-antipruritic-astringent-anti-inflammatory drug, drug for parasitic dermatic disease, haemostatic drug, gout remedy, diabetes drug, antineoplastic drug, antibiotic, chemotherapeutic drug, narcotic drug, stop smoking aid, anti-schizophrenia drug, antidepressant drug and the like.

The drug preferably has a coefficient of partition (1-octanol/water), i.e., logPow of preferably 0.5-5.5, more preferably 1.0-5.0. The drug preferably has a molecular weight of not more than 500, more preferably not more than 450.

When the logPow is less than 0.5, the possibility of crystallization of the drug in an adhesive layer may increase since the hydrophilicity of the drug is high. When the logPow exceeds 5.5, the possibility of crystallization of the drug in an adhesive layer is sufficiently small even when the present invention is not applied, since the hydrophobicity of the drug is high. When the molecular weight exceeds 500, however, the solubility of the drug in an adhesive layer or an organic liquid component decreases, and the possibility of crystallization of the drug in an adhesive layer may increase.

As used herein, logPow is an index showing the hydrophilicity-hydrophobicity of a drug, which refers to values calculated using a logP calculation software Cache (registered trade mark, manufactured by FUJITSU) and according to the instructions of the manufacturer.

As the drug, solid drugs and liquid drugs can be mentioned. As used herein, the solid drug means a drug that is solid at room temperature (25° C.), namely, a drug having a melting point higher than 25° C. In the present invention that uses a solid drug, separation from an adhesive layer, namely, crystal growth in an adhesive layer, can be advantageously suppressed. The liquid drug here means a drug that is liquid at room temperature (25° C.), namely, a drug having a melting point of not more than 25° C. In the present invention that uses a liquid drug, separation from an adhesive layer, namely, bleeding of the drug from an adhesive layer can be advantageously suppressed. The melting point here means values measured by DSC, model number DSC6220 (manufactured by Seiko Instruments Inc. (SII)), where the measurement conditions are as follows: in an aluminum container (open type), a specimen is subjected to temperature rise at 10° C./min and the melting peak temperature is measured.

As the drug, fentanyls are preferable since they can afford analgesic adhesive preparations for terminal cancer patients. The fentanyls here include fentanyl, sufentanyl, and pharmaceutically acceptable salts thereof.

The proportion of a drug in an adhesive layer is not particularly limited as long as it affords the effect of the transdermal absorption drug and does not impair the adhesion property of an adhesive layer. It is preferably 0.1-10 wt %, more preferably 0.5-5 wt %, relative to the weight of an adhesive layer. When it is less than 0.1 wt %, the treatment effect may be insufficient, and when it is higher than 10 wt %, crystallization may occur and skin irritation may be developed.

The organic liquid component is not particularly limited as long as it shows flowability at ambient temperature (25° C.). Examples thereof include polyvalent alcohols such as glycols such as ethylene glycol, diethylene glycol, propylene glycol, dipropylene glycol, tripropylene glycol, triethylene glycol, polyethylene glycol, polypropylene glycol and the like, and glycerol and the like; fats and oils such as olive oil, castor oil, lanolin and the like; hydrocarbons such as squalene, liquid paraffin; various surfactants; polyvalent alcohol esters such as glycerol monoesters such as glycerol monooleate, glycerol monocaprylate, glycerol monolaurate, glycerol diesters, glycerol trimesters or mixtures thereof and the like; fatty acid alkyl esters; ethoxylated stearyl alcohols; alcohols such as long chain alcohol and the like; higher fatty acids such as oleic acid, caprylic acid; pyrrolidones such as N-methylpyrrolidone, N-dodecylpyrrolidone; sulfoxides such as decylmethylsulfoxide; 1,3-butanediol and the like, which may be used alone or in a mixture of two or more kinds thereof.

To achieve a drug transdermal absorption-promoting effect, fatty acid alkyl ester is preferable, and to achieve a drug dissolution-aiding effect, long chain alcohol is preferable. To suppress separation of a drug from an adhesive layer while affording a sufficient transdermal drug absorption-promoting effect, a combined use of fatty acid alkyl ester and long chain alcohol is preferable. The long chain alcohol here means an alcohol having not less than 16 carbon atoms.

A fatty acid alkyl ester made of a fatty acid having an unnecessarily many or small carbon number may show poor compatibility with the aforementioned synthetic rubber and the like, or volatilized in a heating step during formulation of a preparation. In addition, one made of a fatty acid having a double bond in a molecule may undergo oxidative decomposition and the like to cause problems in the preservation stability.

As the fatty acid alkyl ester, therefore, a fatty acid alkyl ester made of a saturated or unsaturated higher fatty acid preferably having 12-16, more preferably 12-14, carbon atoms, and a saturated or unsaturated lower monohydroxy alcohol preferably having 1-4 carbon atoms is preferably adopted. Examples of preferable higher fatty acid include lauric acid (C12), myristic acid (C14) and palmitic acid (C16), particularly myristic acid and palmitic acid. In addition, examples of the lower monohydroxy alcohol include methyl alcohol, ethyl alcohol, propyl alcohol and butyl alcohol, which may be straight chain alcohol or branched alcohol, particularly preferably isopropyl alcohol. Accordingly, examples of the most preferable fatty acid alkyl ester include isopropyl myristate and isopropyl palmitate.

Examples of the long chain alcohol include saturated or unsaturated, branched or straight chain alcohol, and branched type is preferable in view of the compatibility with synthetic rubbers. From the aspect of preservation stability, a saturated type is preferable. Examples of such long chain branched alcohol include long chain branched alcohol preferably having 16-22, more preferably 18-20, carbon atoms. When the carbon number is lower than 16, the compatibility with sunthetic rubber decreases since the hydrophilicity increases, and oozing out from an adhesive layer and the like may occur. When the carbon number exceeds 22, the drug dissolution-aiding effect may be degraded since the hydrophobicity increases. Therefore, isostearyl alcohol (C18), octyldodecanol (C20) and the like are specifically preferable.

To sufficiently dissolve a drug in an adhesive layer and suppress crystallization thereof, the total proportion of these organic liquid components in the adhesive layer is preferably 20 wt % or above, more preferably more than 20 wt %, relative to the total weight of the adhesive layer. When an organic liquid component of this level is added to a conventional adhesive layer, the shape of the adhesive layer is difficult to maintain, and oozing from the adhesive layer may occur during preservation of the adhesive preparation. However, the adhesive preparation of the present invention can contain 20 wt % or more of an organic liquid component relative to the total weight of the adhesive layer while suppressing oozing from the adhesive layer.

On the other hand, since the shape of an adhesive layer cannot be retained easily when the amount of the organic liquid component is too high, its content is preferably less than 50 wt %. Since a greater content of long chain alcohol in an adhesive layer affords a higher solubility of a drug, it is considered that the adhesive layer can dissolve a large amount of a drug, and is advantageously associated with a lower possibility of separation of a drug from the adhesive layer during preservation. While an adhesive layer can dissolve a large amount of a drug and shows a lower possibility of separation of a drug from the adhesive layer during preservation, it has been clarified that, unpredictably, a long chain alcohol contained in a proportion of not less than 7.5 wt % of the adhesive layer relative to the total weight remarkably decreases the skin permeability of the drug. The decrease mechanism is not bound by theory, and is believed to be caused by interactions of the properties of a drug, preferably fentanyls, more preferably fentanyl, and those of long chain alcohol. Therefore, the proportion of a long chain alcohol in an adhesive layer is preferably greater than 0 wt % and less than 7.5 wt %, more preferably not more than 6.5 wt %, and most preferably not more than 5.5 wt %, relative to the total weight of the adhesive layer.

On the other hand, although fatty acid alkyl ester was assumed to have no drug dissolution-aiding effect, it unexpectedly exhibited a drug dissolution-aiding, effect, though lower than that by long chain alcohol. While only one kind thereof may be used at this time, a combination of two or more kinds thereof provides an effect of decreasing the impurity derived from respective fatty acid alkyl esters.

The weight ratio is not particularly limited when two or more kinds of fatty acid alkyl esters are used. In the case of using two kinds, the ratio is preferably 100:1-1:100, more preferably 10:1-1:10, most preferably 2:1-1:2.

Examples of the tackifier include polybutenes, rosin resin, terpene resin, petroleum resin, coumarone resin and the like. A tackifier may be used alone or in a combination of two or more kinds thereof. The proportion of a tackifier in the adhesive layer is preferably 5-50 wt %, more preferably 10-40 wt %, most preferably 16-28 wt %, relative to the total weight of the adhesive layer. When the proportion of the tackifier is less than 5 wt %, the tackiness may be insufficient, and when it exceeds 50 wt %, the adhesive layer sometimes unpreferably shows a tendency toward breakage.

The adhesive constituting the adhesive layer may contain other additives as an optional component (e.g., surfactants such as glycerol fatty acid ester, sorbitan fatty acid ester and the like, organic solvents with a high boiling point such as dimethyl sulfoxide, N-methylpyrrolidone and the like, absorption promoters such as pyrrolidone carboxylate, and the like), as long as they do not inhibit the effect of the present invention. The proportion of an additive as an optional component is preferably 0-15 wt % in total relative to the total weight of the adhesive layer. The thickness of the adhesive layer is generally 30-300 µm, preferably 60-180 µm.

While a support to be used for the present invention is not particularly limited, one substantially impermeable to a drug and the like, in other words, one that does not permit a decrease in the content of a drug (active ingredient), an additive and the like in the adhesive layer, which are lost from the back face through the support, is preferable.

As the support, for example, polyester, nylon, Saran (registered trademark), polyethylene, polypropylene, polyvinyl chloride, ethylene-ethyl acrylate copolymer, polytetrafluoroethylene, Surlyn (registered trademark), independent film such as metal foil and the like, or a laminate film thereof and the like can be used.

From among these, the support is preferably a laminate film of a non-porous plastic film made of the above-mentioned material and a porous film, to improve adhesive strength (anchor strength) thereof with an adhesive layer. In this case, the adhesive layer is preferably formed on the side of the porous film.

As such porous film, one capable of improving the anchor strength with the adhesive layer is adopted. Specific examples include paper, woven fabric, non-woven fabric, knitted fabric, sheet with mechanical perforation treatment and the like. Of these, paper, woven fabric and non-woven fabric are particularly preferable from the aspect of handling property and the like.

The porous film preferably has a thickness of 10-200 µm from the aspects of improvement of anchor strength, flexibility of the whole adhesive preparation, adhesion operability and the like. In the case of a thin preparation such as a plaster type and an adhesive tape type, a preferable thickness is within the range of 10-100 µm. In addition, when woven fabric and non-woven fabric are used as porous films, the fabric weight is preferably 5-30 g/m², more preferably 6-15 g/m².

The most preferable support in the present invention is a laminate film made of a 1.5-6 µm-thick polyester film (preferably polyethylene terephthalate film) and a polyester (preferably polyethylene terephthalate) non-woven fabric (fabric weight 6-12 g/m²).

The adhesive preparation of the present invention preferably has a release liner laminated on an adhesive face to protect the face of the adhesive layer until use.

The release liner is not particularly limited as long as it can be release-treated, and secures sufficiently light release force. For example, films of polyester, polyvinyl chloride, polyvinylidene chloride, polyethylene terephthalate and the like, paper such as high-quality paper, glassine paper and the like, or a laminate film of high-quality paper, glassine paper and the like with polyolefin and the like can be used after a release treatment by applying silicone resin, fluororesin and the like to the surface to be in contact with an adhesive layer. The thickness of the release liner is generally 10-200 µm, preferably 25-100 µm.

The release liner of the present invention is preferably made of a polyester (particularly, polyethylene terephthalate) resin, from the aspects of barrier property and cost. In this case, moreover, one having a thickness of about 25-100 µm is more preferable from the aspect of handling property.

The shape of the adhesive preparation of the present invention is not particularly limited and, for example, tape, sheet, reservoir and the like can be employed.

The adhesive preparation of the present invention can be produced by, for example, dissolving the first synthetic rubber, a drug, an organic liquid component and a tackifier in a suitable solvent such as toluene and the like, applying a solvent solution of the obtained composition for forming an adhesive layer to a release liner and drying same to form an adhesive layer, and laminating a support on the adhesive layer.

In addition, the adhesive preparation of the present invention can be produced by, for example, directly applying the above-mentioned solvent solution of a composition for forming an adhesive layer to a support, drying same to form an adhesive layer on the support.

The adhesive preparation of the present invention can be used by peeling off the release liner just before use and adhering the exposed adhesive face to the skin and the like.

While the dose of the adhesive preparation of the present invention varies depending on the age, body weight, symptom and the like of the patients, generally, a preparation containing 0.1-100 mg of a drug is applied to 1-100 cm² of the skin of an adult about 1-7 times in 7 days.

EXAMPLES

The present invention is explained in detail in the following by referring to Examples, which are not to be construed as limitative. Unless otherwise specified, the proportion of each component is shown in wt % relative to the total weight of the adhesive layer. The starting materials and abbreviations thereof to be used in the Examples and the like are as follows.

drug: fentanyl
coefficient of partition logPow=3.78, molecular weight 336.47, melting point 83-84° C.
A: 2-methylpropene-polymer having a viscosity average molecular weight of 4,000,000
B: 2-methylpropene-polymer having a viscosity average molecular weight of 55,000
C: 2-methylpropene-polymer having a viscosity average molecular weight of 800,000
D: 2-methylpropene-polymer having a viscosity average molecular weight of 2,600,000
E: 2-methylpropene-polymer having a viscosity average molecular weight of 2,120,000
F: 2-methylpropene-polymer having a viscosity average molecular weight of 1,660,000

G: 2-methylpropene-polymer having a viscosity average molecular weight of 1,250,000
H: 2-methylpropene-polymer having a viscosity average molecular weight of 900,000
tackifier: polybutene
IPM: isopropyl myristate
IPP: isopropyl palmitate
ODO: octyldodecanol Preliminary Experimental Examples 1-2, Examples 1-12 and Comparative Examples 1-7

According to the component ratios shown in Table 1, a solution of a composition for adhesive layer formation in toluene was prepared, and the obtained solution was applied to a polyethylene terephthalate (PET) liner (thickness 75 μm) after a silicone release treatment in such a manner that the thickness after drying would be as shown in Table 1. The liner was dried in a circulating-air oven at 100° C. for 5 min to form an adhesive layer. The adhesive layer was adhered to a PET support to give a sheet-like adhesive preparation.

The adhesive preparations obtained in Preliminary Experimental Examples 1-2, Examples 1-12 and Comparative Examples 1-7 were observed for oozing and crystal, and the shear adhesion was measured. The observation results are shown in Table 1.

TABLE 1

|  | fentanyl | synthetics rubber first | synthetics rubber non-first and non-second | synthetics rubber second | tackifier | fatty acid ester 1 | fatty acid ester 2 | long chain alcohol | organic liquid component total amount | thickness (μm) of adhesive layer | drug content (mg/cm$^2$) | oozing | shear adhesion [min] | crystal | permeability Flux (max) (relative value) |
|---|---|---|---|---|---|---|---|---|---|---|---|---|---|---|---|
| Prelim. Exp. Ex. 1 | — | A 23.24 | — | B 34.85 | 20.91 | IPM 10 | IPP 10 | ODO 1 | 21 | 100 | — | ○ | — | — | — |
| Prelim. Exp. Ex. 2 | — | — | C 23.24 | B 34.85 | 20.91 | IPM 10 | IPP 10 | ODO 1 | 21 | 100 | — | X | — | — | — |
| Ex. 1 | 2.5 | A 17.25 | — | B 23.0 | 17.25 | IPM 15 | IPP 10 | ODO 15 | 40 | 100 | 2.5 | ○ | — | ○ | — |
| Ex. 2 | 2.0 | A 16.2 | — | B 23.2 | 18.6 | IPM 15 | IPP 15 | ODO 10 | 40 | 125 | 2.5 | ○ | — | ○ | — |
| Ex. 3 | 3.0 | A 17.0 | — | B 28.4 | 25.6 | IPM 6 | IPP 10 | ODO 10 | 26 | 83 | 2.5 | ○ | — | ○ | — |
| Ex. 4 | 3.0 | A 17.4 | — | B 24.8 | 19.8 | IPM 20 | IPP 10 | ODO 5 | 35 | 83 | 2.5 | ○ | — | ○ | 148 |
| Ex. 5 | 2.0 | A 19.5 | — | B 29.6 | 28.9 | IPM 10 | IPP 10 | — | 20 | 125 | 2.5 | ○ | 3.3 | ○ | 165 |
| Ex. 6 | 2.5 | A 18.9 | — | B 28.7 | 27.9 | IPM 10 | IPP 10 | ODO 2 | 22 | 100 | 2.5 | ○ | 5.9 | ○ | 152 |
| Ex. 7 | 3.0 | A 19.1 | — | B 27.9 | 26.5 | IPM 10 | IPP 10 | ODO 3.5 | 23.5 | 83 | 2.5 | ○ | 4.0 | ○ | 133 |
| Ex. 8 | 3.0 | D 19.1 | — | B 27.9 | 26.5 | IPM 10 | IPP 10 | ODO 3.5 | 23.5 | 83 | 2.5 | ○ | 2.1 | ○ | — |
| Ex. 9 | 3.0 | E 19.1 | — | B 27.9 | 26.5 | IPM 10 | IPP 10 | ODO 3.5 | 23.5 | 83 | 2.5 | ○ | 1.2 | ○ | — |
| Ex. 10 | 3.0 | F 19.1 | — | B 27.9 | 26.5 | IPM 10 | IPP 10 | ODO 3.5 | 23.5 | 83 | 2.5 | ○ | 0.7 | ○ | — |
| Ex. 11 | 3.5 | A 19.17 | — | B 26.98 | 24.85 | IPM 10 | IPP 10 | ODO 5.5 | 25.5 | 71 | 2.5 | ○ | 3.7 | ○ | 142 |
| Ex. 12 | 4.0 | A 19.2 | — | B 26.0 | 23.3 | IPM 10 | IPP 10 | ODO 7.5 | 27.5 | 63 | 2.5 | ○ | 3.1 | ○ | 117 |
| Com. Ex. 1 | 1.7 | — | C 24.50 | B 36.75 | 22.05 | IPM 10 | — | ODO 5 | 15 | 147 | 2.5 | X | — | ○ | 100 |
| Com. Ex. 2 | 2.5 | — | C 25.8 | B 38.7 | 18 | IPM 10 | — | ODO 5 | 15 | 100 | 2.5 | X | — | X | — |
| Com. Ex. 3 | 2.5 | — | C 28.7 | B 43.0 | 25.6 | — | — | — | 0 | 100 | 2.5 | ○ | — | X | — |
| Com. Ex. 4 | 3.0 | — | C 25.6 | B 38.4 | 23 | — | IPP 5 | ODO 5 | 10 | 83 | 2.5 | ○ | — | X | — |
| Com. Ex. 5 | 3.0 | — | C 27.05 | B 40.60 | 24.35 | IPM 5 | — | — | 5 | 83 | 2.5 | ○ | — | X | — |
| Com. Ex. 6 | 3.0 | — | G 19.1 | B 27.9 | 26.5 | IPM 10 | IPP 10 | ODO 3.5 | 23.5 | 83 | 2.5 | X | 0.4 | ○ | — |
| Com. Ex. 7 | 3.0 | — | H 19.1 | B 27.9 | 26.5 | IPM 10 | IPP 10 | ODO 3.5 | 23.5 | 83 | 2.5 | X | 0.5 | ○ | — |

Unless specifically indicated, the unit is wt % relative to the weight of an adhesive layer.

<Test Method>
(1) Oozing

Preparations preserved at room temperature for 3 months were evaluated according to the following criteria when taken out from a packing material.

○: Almost no oozing was observed, and preparation could be taken out easily from a packing material without sticking.

x: Oozing was observed, and preparation stuck to a packing material and could not be taken out easily.

(2) Crystal

Adhesive preparations preserved at room temperature for 3 months were observed visually and with a microscope, and evaluated according to the following criteria.

○: Drug was not crystallized.

x: Drug was crystallized.

(3) Shear Adhesion

In a room at 23±2° C., 50±10% RH (relative humidity), an adhesive face of a test piece (10 mm width) was lightly adhered to a clean phenol resin board as a test plate, and press-adhered by one reciprocation of a 850 g adhesion roller on the test piece. The compression area was set to 200 mm². The test plate was stood for 30 min in a shear adhesion testing machine set to a 40±2° C. environment, and one end of the test plate was held to hang it perpendicularly. A 150 g load was applied to the lower end and the time (min) before dropping was measured. The failure was confirmed to be of a cohesive failure mode for all the test pieces measured at this time.

The results of Preliminary Experimental Examples 1 and 2 free of a drug are first explained.

In Preliminary Experimental Example 1 using A as the first synthetic rubber, almost no oozing was observed even when the total ratio of the organic liquid component was 20 wt % or above. In Preliminary Experimental Example 2, which is the same as Preliminary Experimental Example 1 except that C was used instead of A, however, oozing was observed. Therefore, it has been clarified that use of a first synthetic rubber having a viscosity average molecular weight of 1,600,000-6,500,000 almost completely prevents oozing even when a large amount of an organic liquid component is contained in an adhesive layer.

The results of Examples and Comparative Examples containing a drug are now explained.

Examples 1-12 using A as the first synthetic rubber, wherein the total amount of the organic liquid component was not less than 20 wt %, were free of oozing and crystallization of a drug. However, in Comparative Examples using C instead of A, oozing was developed (Comparative Examples 1 and 2) and crystallization of a drug occurred (Comparative Examples 2-5), despite the fact that the total amount of an organic liquid component was not more than 20 wt %. In Comparative Examples 6 and 7 using G or H instead of A, oozing was developed and the shear adhesion was low. In Examples 7-10 and Comparative Examples 6-7 containing 23.5 wt % of an organic liquid component, Examples containing the first synthetic rubber component having a viscosity average molecular weight of not less than 1,600,000, particularly not less than 2,000,000, had sufficient shear adhesion. On the other hand, Comparative Examples 6-7 containing a synthetic rubber component having a viscosity average molecular weight of less than 1,600,000 showed insufficient shear adhesion. In Examples 5-7 and 11-12, moreover, the shear adhesion was high, and the adhesive layers thereof retained their shape extremely well, and were free of possibility of oozing during storage of the adhesive preparation and adhesive residue on the skin surface upon peeling off of the adhesive preparation from the skin.

Of the adhesive preparations free of crystallization in Table 1, the adhesive preparations obtained in Examples 4-7, 11-12 and Comparative Example 1 were subjected to a human skin permeability test. The test results are shown in Table 1 (shown above).

<Test Method>

The above-mentioned adhesive preparation was cut into a 12 mmφ circle and applied to the stratum corneum of the human skin. The dermal layer side was set on a Franz diffusion cell, and a test was performed using physiological saline (0.9 wt % NaCl+0.01 wt % $NaN_3$, 32° C.) as a receptor solution. The receptor solution was sampled at given time intervals and the weight of the drug in the sample solution was quantified by an HPLC method, based on which the maximum flux up to 48 hr was calculated. The maximum flux is a relative value when Comparative Example 1 is 100.

When the maximum flux of Comparative Example 1 is 100, Examples 4-7 and 11, wherein the proportion of ODO is not more than 7.5 wt %, showed a high value of 133-165. In contrast, Example 12, wherein the proportion of ODO is 7.5 wt %, showed a tendency toward a lower maximum flux of 117. Therefore, to achieve particularly high skin permeability while suppressing crystallization of a solid drug in an adhesive layer, it was preferable to set the total amount of the organic liquid component to not less than 20 wt %, and long chain alcohol to not less than 0 wt % and not more than 7.5 wt %.

A rabbit primary skin irritation test was performed using the adhesive preparations obtained in Examples 5 and 7, and Comparative Example 1. The rabbit primary skin irritation test was performed according to the Draze method.

The test results are shown in Table 2.

TABLE 2

| | P.I.I |
|---|---|
| Example 5 | 0.9 (weak skin stimulation) |
| Example 7 | 0.9 (weak skin stimulation) |
| Comparative Example 1 | 1.2 (weak skin stimulation) |

The adhesive preparations of Examples 5 and 7 showed low skin stimulation as compared to the adhesive preparation of Comparative Example 1. The P.I.I. (primary skin irritation index) of the adhesive preparations of Examples 5 and 7 was not more than 2, which is the level of a weak stimulant, and the skin stimulation was sufficiently low.

The adhesive preparations obtained in Examples 5 and 7 were subjected to a preservation stability test.

<Test Method>

The adhesive preparations obtained in Examples 5 and 7 were packaged with a polyethylene terephthalate/aluminum/acrylonitrile resin packing material, and preserved at 50° C. for 2 months. The solid drug weight after the preservation period was quantified by HPLC, and the proportion of the drug weight after preservation relative to the initial drug weight was calculated in a percentage. The results are shown in Table 3.

TABLE 3

| | amount of drug (%) after preservation |
|---|---|
| Example 5 | 98.9 |
| Example 7 | 98.8 |

All adhesive preparations of Examples 5 and 7 showed almost 100%, and the adhesive preparation of the present invention showed superior preservation stability.

This application is based on a patent application No. 2007-050379 filed in Japan, the contents of which are incorporated in full herein by this reference.

The invention claimed is:

1. An adhesive preparation having an adhesive layer on at least one surface of a support, wherein the adhesive layer comprises a first synthetic rubber, which is 2-methylpropene-polymer having a viscosity average molecular weight of 3,000,000-5,000,000, a drug, which is a fentanyl selected from fentanyl, sufentanyl, and pharmaceutically acceptable salts thereof, an organic liquid component and a tackifier, which is one or more kinds selected from polybutenes, rosin resin, terpene resin, petroleum resin and coumarone resin, wherein the organic liquid component comprises a fatty acid alkyl ester and a long chain alcohol, the long chain alcohol is contained in a proportion of more than 0 wt % and less than 7.5 wt % relative to the total weight of the adhesive layer, and the drug is contained in a proportion of 0.1-10 wt % relative to the total weight of the adhesive layer.

2. The adhesive preparation of claim 1, wherein the organic liquid component is contained in the adhesive layer in a proportion of 20 wt % or above relative to the total weight of the adhesive layer.

3. The adhesive preparation of claim 1, wherein the fatty acid alkyl ester comprises two or more kinds thereof.

* * * * *

UNITED STATES PATENT AND TRADEMARK OFFICE
CERTIFICATE OF CORRECTION

PATENT NO. : 8,309,119 B2
APPLICATION NO. : 12/071867
DATED : November 13, 2012
INVENTOR(S) : Masato Nishimura Page 1 of 1

It is certified that error appears in the above-identified patent and that said Letters Patent is hereby corrected as shown below:

Column 14, line 3, change "a long chain alcohol, the long chain alcohol" to -- octyldodecanol, wherein the octyldodecanol --;

line 7, change "." to -- , wherein the adhesive layer further comprises a second synthetic rubber, which is 2-methylpropene-polymer having a viscosity average molecular weight of 40,000-85,000, the first synthetic rubber is contained in a proportion of 10-30 wt% relative to the total weight of the adhesive layer, the second synthetic rubber is contained in a proportion of 10-40 wt% relative to the total weight of the adhesive layer, the fentanyl selected from fentanyl, sufentanyl, and pharmaceutically acceptable salts thereof is contained in a proportion of 0.5-5 wt% relative to the total weight of the adhesive layer, and the tackifier is contained in a proportion of 10-40 wt% relative to the total weight of the adhesive layer. --

Signed and Sealed this
Ninth Day of April, 2013

Teresa Stanek Rea
*Acting Director of the United States Patent and Trademark Office*